United States Patent
Jin et al.

(10) Patent No.: US 9,655,580 B2
(45) Date of Patent: May 23, 2017

(54) SYSTEMS AND METHODS FOR METAL ARTIFACT REDUCTION

(71) Applicant: GENERAL ELECTRIC COMPANY, Schenectady, NY (US)

(72) Inventors: Yannan Jin, Niskayuna, NY (US); Bruno Kristiaan Bernard De Man, Clifton Park, NY (US); Ge Wang, Loudonville, NY (US); Yan Xi, Troy, NY (US)

(73) Assignee: General Electric Company, Niskayuna, NY (US)

( * ) Notice: Subject to any disclaimer, the term of this patent is extended or adjusted under 35 U.S.C. 154(b) by 52 days.

(21) Appl. No.: 14/920,991

(22) Filed: Oct. 23, 2015

(65) Prior Publication Data
US 2016/0117850 A1    Apr. 28, 2016

Related U.S. Application Data

(60) Provisional application No. 62/068,053, filed on Oct. 24, 2014.

(51) Int. Cl.
G06K 9/00    (2006.01)
A61B 6/00    (2006.01)
(Continued)

(52) U.S. Cl.
CPC ............ *A61B 6/5258* (2013.01); *A61B 6/03* (2013.01); *A61B 6/482* (2013.01); *G06T 5/005* (2013.01);
(Continued)

(58) Field of Classification Search
None
See application file for complete search history.

(56) References Cited

U.S. PATENT DOCUMENTS 8,165,264 B2    4/2012    Zou
8,233,586 B1    7/2012    Boas
(Continued)

FOREIGN PATENT DOCUMENTS

CN    103700124 A    4/2014

OTHER PUBLICATIONS

The impact of dual energy CT on pseudoenhancement of kidney lesions, by Muller et al., Proc. of SPIE vol. 7622, 762231, Medical Imaging 2010.*
(Continued)

*Primary Examiner* — Vikkram Bali
(74) *Attorney, Agent, or Firm* — Pabitra K. Chakrabarti

(57) ABSTRACT

A method includes receiving, with at least one processor, a first projection dataset corresponding to X-rays at a first energy level projected towards a subject at a first set of view angles and receiving, with the at least one processor, a second projection dataset corresponding to X-rays at a second energy level projected towards the subject at a second set of view angles. The method further includes identifying, with the at least one processor, a metal trace from at least one of the first projection dataset and the second projection dataset. Moreover, the method includes converting, with the at least one processor, at least a portion of the first projection dataset to a pseudo dataset at the second energy level. The method also includes generating, with the at least one processor, a final image of the subject based on the second projection dataset, the pseudo dataset, and the metal trace.

25 Claims, 12 Drawing Sheets

(51) Int. Cl.
  *A61B 6/03* (2006.01)
  *G06T 5/00* (2006.01)
  *G06T 5/50* (2006.01)
  *G06T 11/00* (2006.01)
(52) U.S. Cl.
  CPC .............. *G06T 5/50* (2013.01); *G06T 11/005* (2013.01); *A61B 6/5205* (2013.01); *G06T 2207/10081* (2013.01); *G06T 2207/10144* (2013.01); *G06T 2207/20221* (2013.01); *G06T 2207/30004* (2013.01); *G06T 2211/408* (2013.01)

(56) References Cited

U.S. PATENT DOCUMENTS

| | | |
|---|---|---|
| 8,503,750 B2 | 8/2013 | Benson et al. |
| 2008/0240531 A1 | 10/2008 | Sasaki et al. |
| 2010/0215233 A1* | 8/2010 | Hsieh ................... A61B 6/032 382/131 |
| 2011/0081071 A1* | 4/2011 | Benson ................. G06T 11/005 382/154 |
| 2011/0206258 A1* | 8/2011 | Chen .................... G06T 11/005 382/131 |
| 2013/0070991 A1 | 3/2013 | Yang et al. |
| 2014/0056497 A1* | 2/2014 | Hsieh ..................... G06T 5/005 382/131 |
| 2014/0193086 A1 | 7/2014 | Zhang et al. |
| 2014/0198892 A1 | 7/2014 | Yamakawa et al. |
| 2016/0238717 A1* | 8/2016 | Abraham ................ G01T 1/17 |

OTHER PUBLICATIONS

Boas et al., "CT artifacts: Causes and reduction techniques", Imaging in Medicine, vol. 4, Issue 2, 2012, pp. 229-240.

Rajendran et al., "Reducing beam hardening effects and metal artefacts in spectral CT using Medipix3RX", Journal of Instrumentation, vol. 9, 2014, pp. 1-14.

* cited by examiner

300 

Receive a first projection dataset corresponding to X-rays at a first energy level projected towards a subject at a first set of view angles 302

Receive a second projection dataset corresponding to X-rays at a second energy level projected towards the subject at a second set of view angles 304

Identify a metal trace from at least one of the first projection dataset and the second projection dataset 306

Convert at least a portion of the first projection dataset to a pseudo dataset at the second energy level 308

Generate a final image of the subject based on the second projection dataset, the pseudo dataset, and the metal trace 310

Visualize the final image on a display 312

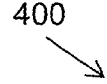

Receive a first projection dataset corresponding to X-rays at a first energy level projected towards a subject at a first set of view angles 402

Receive a second projection dataset corresponding to X-rays at a second energy level projected towards the subject at a second set of view angles 404

Reconstruct a first image based on the first projection dataset 406

Identify a metal mask and a neighborhood mask from the first image 408

Detect a metal trace and a neighborhood trace in the first projection dataset based on the metal mask and the neighborhood mask 410

Convert at least a portion of the first projection dataset to a pseudo dataset at the second energy level 412

Generate a final image of the subject based on the second projection dataset, the pseudo dataset and the metal trace 414

FIG. 4

SYSTEMS AND METHODS FOR METAL ARTIFACT REDUCTION

CROSS REFERENCE TO RELATED APPLICATIONS

This non-provisional application claims the benefit of priority under 35 U.S.C. §119(e) to U.S. Provisional Patent Application Ser. No. 62/068,053, entitled "CT metal artifact reduction (MAR) using high energy x-rays" filed on Oct. 24, 2014, which is herein incorporated in its entirety by reference.

BACKGROUND

The technology disclosed herein generally relates to Computed Tomography (CT). More specifically, the technology disclosed herein relates to systems and methods for metal artifact reduction in a CT image.

Computed tomography imaging uses X-rays to generate CT images of a subject (e.g., a human patient, a phantom object, and the like). Often, the subject includes metal objects or other high-density objects, for example, metal prostheses, dental implants, surgical clips, and the like. Typically, the presence of a metal object in the subject results in degradation in the quality of the CT images since the metal object has strong absorption of X-rays, causing metal artifacts such as streaks and shadings in the CT images that obscure other portions of the subject. For example, a titanium hip in a human patient may cause photon starvation and lead to metal artifacts in a CT image of the human patient. In such an example, the metal artifacts limit the assessment of soft tissue and skeletal portions surrounding the metallic hip in the CT image and may lead to a misdiagnosis of the subject. Prior methods of metal artifact reduction often include corrections to the corrupted image data based on assumptions and approximations. However, such prior methods based on assumptions and approximations tend to introduce new artifacts and hence fail to generate CT images of satisfactory quality.

BRIEF DESCRIPTION

In accordance with one aspect of the present specification, a method includes receiving, with at least one processor, a first projection dataset corresponding to X-rays at a first energy level projected towards a subject at a first set of view angles and receiving, with the at least one processor, a second projection dataset corresponding to X-rays at a second energy level projected towards the subject at a second set of view angles. In addition, the method includes identifying, with the at least one processor, a metal trace from at least one of the first projection dataset and the second projection dataset. The method also includes converting, with the at least one processor, at least a portion of the first projection dataset to a pseudo dataset at the second energy level. The method further includes generating, with the at least one processor, a final image of the subject based on the second projection dataset, the pseudo dataset, and the metal trace. A computer program product including non-transitory computer readable medium, which in turn includes one or more tangible media, where the one or more tangible media include code adapted to perform the method is also presented.

In accordance with another aspect of the present specification, a system is presented. The system includes at least one processor. Further, the system includes a communication subunit configured to receive a first projection dataset corresponding to X-rays at a first energy level projected towards a subject at a first set of view angles and receive a second projection dataset corresponding to X-rays at a second energy level projected towards the subject at a second set of view angles. The system further includes a mask subunit configured to identify a metal trace from at least one of the first projection dataset and the second projection dataset. Moreover, the system includes a conversion subunit configured to convert at least a portion of the first projection dataset to a pseudo dataset at the second energy level. Additionally, the system includes a final image subunit configured to generate a final image of the subject based on the second projection dataset, the pseudo dataset, and the metal trace, where one or more of the communication subunit, the mask subunit, the conversion subunit, and the final image subunit are executable by the at least one processor.

In accordance with yet aspect of the present specification, an imaging system is presented. The system includes a CT scanner configured to project X-rays at a first energy level towards a subject at a first set of view angles and project X-rays at a second energy level towards the subject at a second set of view angles. The CT scanner is further configured to generate a first projection dataset corresponding to the X-rays at the first energy level and generate a second projection dataset corresponding to the X-rays at the second energy level. Furthermore, the system includes a controller communicatively coupled with the CT scanner. The controller includes at least one processor. In addition, the controller includes communication subunit configured to receive a first projection dataset corresponding to X-rays at a first energy level projected towards a subject at a first set of view angles and receive a second projection dataset corresponding to X-rays at a second energy level projected towards the subject at a second set of view angles. The controller further includes a mask subunit configured to identify a metal trace from at least one of the first projection dataset and the second projection dataset. Moreover, the controller includes a conversion subunit configured to convert at least a portion of the first projection dataset to a pseudo dataset at the second energy level. Additionally, the controller includes a final image subunit configured to generate a final image of the subject based on the second projection dataset, the pseudo dataset, and the metal trace, where one or more of the communication subunit, the mask subunit, the conversion subunit, and the final image subunit are executable by the at least one processor.

DRAWINGS

These and other features, aspects, and advantages of the present invention will become better understood when the following detailed description is read with reference to the accompanying drawings in which like characters represent like parts throughout the drawings, wherein:

FIGS. 2-11 are flow diagrams illustrating exemplary methods for metal artifact reduction, in accordance with aspects of the present specification.

DETAILED DESCRIPTION

In the following specification and the claims, reference will be made to a number of terms, which shall be defined to have the following meanings.

The singular forms "a," "an," and "the" include plural references unless the context clearly dictates otherwise.

As used herein, the term "non-transitory computer-readable media" is intended to be representative of any tangible computer-based device implemented in any method or technology for short-term and/or long-term storage of information, such as, computer-readable instructions, data structures, program modules and sub-modules, or other data in any device. Therefore, methods described herein may be encoded as executable instructions embodied in a tangible, non-transitory, computer readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and non-volatile media, and removable and non-removable media such as a firmware, physical and virtual storage, a compact disc read only memory, a digital versatile disc, and any other digital source such as a network or the Internet, as well as yet to be developed digital means, with the sole exception being a transitory, propagating signal.

As used herein, the terms "software" and "firmware" are interchangeable, and include any computer program stored in memory for execution by devices that include, without limitation, mobile devices, clusters, personal computers, workstations, clients, and servers.

As used herein, the term "computer" and related terms, e.g., "computing device", are not limited to integrated circuits referred to in the art as a computer, but broadly refers to at least one microcontroller, microcomputer, programmable logic controller (PLC), application specific integrated circuit, and other programmable circuits, and these terms are used interchangeably herein throughout the specification.

Approximating language, as used herein throughout the specification and claims, may be applied to modify any quantitative representation that could permissibly vary without resulting in a change in the basic function to which it is related. Accordingly, a value modified by a term or terms, such as "about" and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

Figure 1:
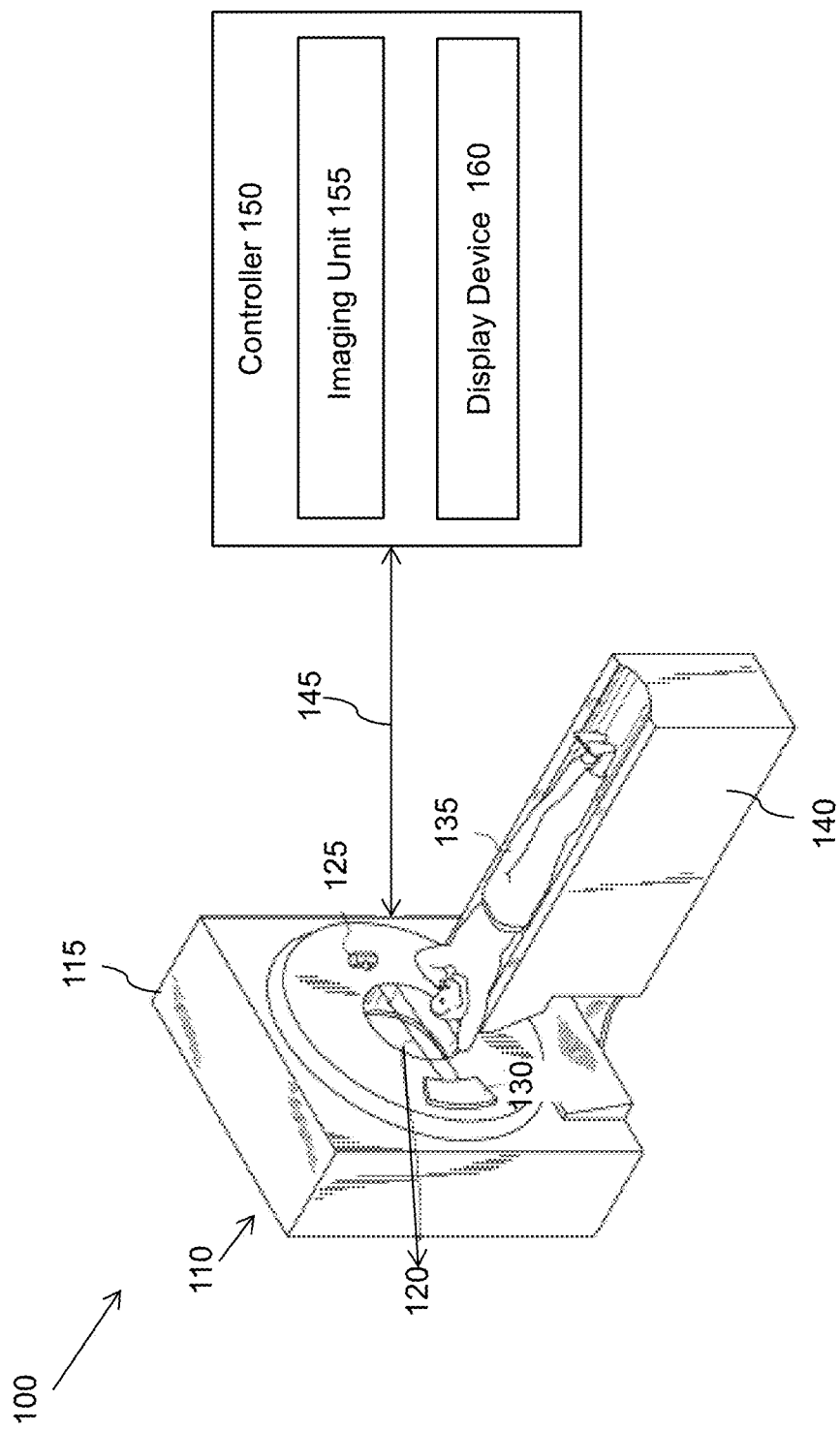
FIG. 1 is a block diagram illustrating an exemplary system for metal artifact reduction, in accordance with aspects of the present specification.

Systems and methods for metal artifact reduction are described herein. FIG. 1 illustrates a block diagram of an exemplary system 100 for metal artifact reduction, in accordance with aspects of the present specification. In the illustrated embodiment, the system 100 includes a CT scanner 110 and a controller 150 that are communicatively coupled to each other. In the embodiment of FIG. 1, the CT scanner 110 and controller 150 are shown as being communicatively coupled via a wired signal line 145. However, in other embodiments, the CT scanner 110 and the controller 150 may be communicatively coupled wirelessly. Although the embodiment of FIG. 1 depicts the CT scanner 110 and the controller 150 as two standalone units, in another embodiment, the controller 150 may be included within the CT scanner 110.

The CT scanner 110 may be any type of scanner that is configured to project X-rays at a plurality of energy levels towards a subject 135 and generate plurality of projection datasets corresponding to the X-rays at the plurality of energy levels. Although the subject 135 is illustrated as a human patient in the embodiment in FIG. 1, in other embodiments the subject 135 may be an animal, an inanimate object, a phantom, and the like. Non-limiting examples of the CT scanner 110 include an axial mode scanner, a helical mode scanner, a single X-ray source scanner, a dual X-ray source scanner, and the like. In the illustrated embodiment, the CT scanner 110 includes a motorized table 140 for disposing the subject 135 in a desired position for scanning. During operation of the system 100, the motorized table 140 may be configured to move into an opening 120 created by a gantry 115.

The gantry 115 includes an X-ray source 125 and an X-ray detector 130 that are positioned on opposite sides of the opening 120. The X-ray source 125 is configured to project X-rays towards the subject 135 at a plurality of energy levels such as 80 peak kilovoltage (kVp), 120 kVp, 160 kVp, 180 kVp, and the like. During operation of the system 100, the X-ray source 125 is configured to rotate around the opening 120 and project the X-rays towards the subject 135 at a plurality of view angles. Further, the X-ray source 120 is configured to switch between projecting X-rays at the plurality of energy levels while rotating around the opening 120. The X-ray detector 130 is configured to rotate in tandem with the X-ray source 125 and receive the X-rays that are attenuated by the subject 135. Further, the X-ray detector 130 is configured to generate a plurality of projection datasets corresponding to the attenuated X-rays at the plurality of energy levels. Also, the X-ray detector 130 is configured to transmit the plurality of projection datasets to the controller 150 via the signal line 145. Although in the illustrated embodiment, the CT scanner 110 includes a single X-ray source 125 for switching between X-rays at the plurality of energy levels, in another embodiment, the CT scanner 110 may include a plurality of X-ray sources for projecting X-rays at the plurality of energy levels.

In one embodiment, the X-ray source 125 is configured to project X-rays at a first energy level towards the subject 135 at a first set of view angles of the plurality of view angles. The X-ray source 125 is further configured to project X-rays at a second energy level towards the subject 135 at a second set of view angles of the plurality of view angles. In such an embodiment, the first energy level may be, for example, 160 kVp, 180 kVp, and the like. Typically, the X-rays generated at the first energy level penetrate high density objects, for example, metal implants, dental implants, surgical clips, and the like. The second energy level is generally lower than the first energy level and may be, for example, 100 kVp, 120 kVp, and the like. Typically, the X-rays generated at the second energy level are used for diagnostic CT imaging of the subject 135. Further, the first set of view angles is different from the second set of view angles. Also, a number of view angles in the first set is lower than a number of view angles in the second set. For example, the number of view angles in the first set may be ten times lower than the number of view angles in the second set. In such an embodiment, the X-ray detector 130 may be configured to generate a first projection dataset and a second projection dataset corresponding to the X-rays at the first energy level and the second energy level respectively. The X-ray detector 130 is further configured to transmit the first and second projection datasets to the controller 150. In one embodiment, where the CT scanner 110 is a dual X-ray source scanner, a first X-ray source may be configured to project X-rays at the first energy level towards the subject 135 at the first set of view angles and a second X-ray source may be configured to project X-rays at the second energy level towards the subject 135 at the second set of view angles The controller 150 may be any type of device that is configured to control the operation of the CT scanner 110 and generate a final image of the subject 135 based on the plurality of the projection datasets. While the focus of the discussion herein is on the generation of the final image of the subject 135, it may be noted that the controller 150 may also perform other control features (for example, controlling scanning parameters, the rotation of the X-ray source 125 and the X-ray detector 130, and the like). In the illustrated embodiment, the controller 150 includes an imaging unit 155 and a display device 160. The imaging unit 150 may be any type of computing device configured to receive the plurality of projection datasets from the CT scanner 110 and generate the final image of the subject 135 based on metal artifact reduction. The imaging unit 155 will be described in further detail with reference to FIG. 2. The display device 160 is configured to receive graphical data from the imaging unit 155 and render the graphical data. For example, the display device 160 may receive graphical data of the final image of the subject 135. The display device 160 then renders the graphical data and displays the final image of the subject 135 to an operator of the system 100.

Figure 2:
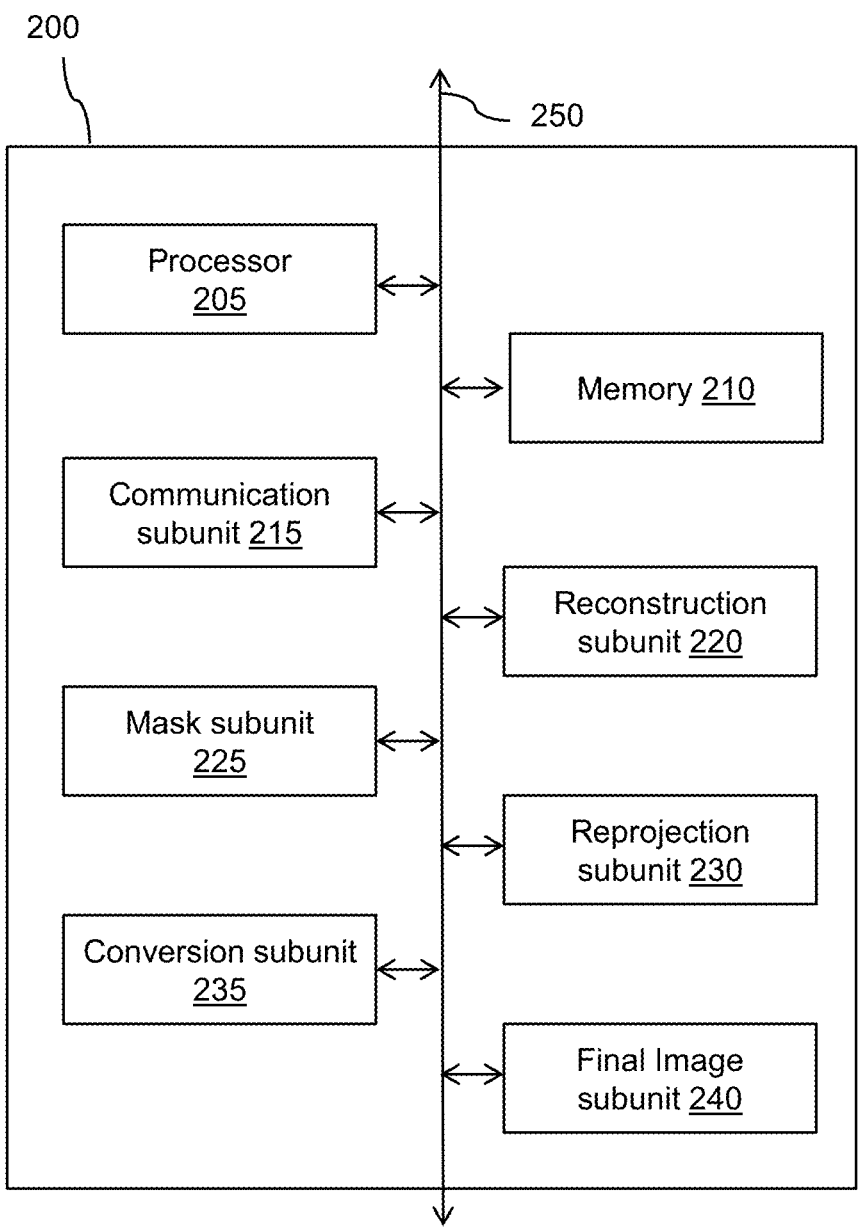

Referring now to FIG. 2, a block diagram of an exemplary imaging unit 200 for use in the system 100 of FIG. 1, in accordance with aspects of the present specification, is depicted. In the illustrated embodiment, the imaging unit 200 includes a processor 205, memory 210, a communication subunit 215, a reconstruction subunit 220, a mask subunit 225, a reprojection subunit 230, a conversion subunit 235, and a final image subunit 240. The processor 205, the memory 210, and the plurality of subunits of the imaging unit 200 are coupled to a bus 250. The bus 250 facilitates communication among the various components of the imaging unit 200.

The processor 205 may include at least one arithmetic logic unit, microprocessor, general purpose controller or other processor arrays configured to perform computations, and/or retrieve data stored in the memory 210. In one embodiment, the processor 205 may be a multiple core processor. The processor 205 processes data signals and may include various computing architectures including a complex instruction set computer (CISC) architecture, a reduced instruction set computer (RISC) architecture, or an architecture implementing a combination of instruction sets. In one embodiment, the processing capability of the processor 205 may support the retrieval of data and transmission of data. In another embodiment, the processing capability of the processor 205 may also perform more complex tasks, including various types of feature extraction, modulating, encoding, multiplexing, and the like. Other type of processors, operating systems, and physical configurations are also envisioned.

The memory 210 may be a non-transitory storage medium. For example, the memory 210 may be a dynamic random access memory (DRAM) device, a static random access memory (SRAM) device, flash memory or other memory devices. The memory 210 may also include a non-volatile memory or similar permanent storage device, and media such as a hard disk drive, a floppy disk drive, a compact disc read only memory (CD-ROM) device, a digital versatile disc read only memory (DVD-ROM) device, a digital versatile disc random access memory (DVD-RAM) device, a digital versatile disc rewritable (DVD-RW) device, a flash memory device, or other non-volatile storage devices.

The memory 210 stores data that is required for the imaging unit 200 to perform associated functions. In one embodiment, the memory 210 stores codes and routines related to one or more subunits of the imaging unit 200. In another embodiment, the memory 210 stores a predetermined distance, a projection domain level look-up table, and an image domain look-up table that are defined by, for example, an administrator of the imaging unit 200 based on previously generated clinical data. The predetermined distance and the look-up tables are described in further detail with reference to the mask subunit 225 and the conversion subunit 235 respectively.

The communication subunit 215 includes codes and routines configured to handle communication between the CT scanner, the display device, and one or more subunits of the imaging unit 200. In one embodiment, the communication subunit 215 includes a set of instructions executable by the processor 205 to provide the functionality for handling communications between a CT scanner, a display device, and one or more subunits of the imaging unit 200. In another embodiment, the communication subunit 215 is stored in the memory 210 and is accessible and executable by the processor 205. In either embodiment, the communication subunit 215 is adapted for communication and cooperation with the processor 205 and the one or more subunits of the imaging unit 200 via the bus 250.

In one embodiment, the communication subunit 215 receives first and second projection datasets from the CT scanner. As noted hereinabove, the first projection dataset corresponds to X-rays at a first energy level projected towards a subject at a first set of view angles. Similarly, the second projection dataset corresponds to X-rays at a second energy level projected towards the subject at a second set of view angles. Further, the first energy level (for example, 160 kVp) is higher than the second energy level (for example, 120 kVp). In such an embodiment, the communication subunit 215 transmits the first and second projection datasets to one or more of the reconstruction subunit 220, the mask subunit 225, the reprojection subunit 230, and the conversion subunit 235. In one embodiment, the first and second projection datasets received from the CT scanner may be in analog form. In such an embodiment, the communication subunit 215 may also be configured to sample and convert the first and second projection datasets to digital form. In another embodiment, the communication subunit 215 receives graphical data for providing a final image of the subject to, for example, a clinician. In such an embodiment, the communication subunit 215 communicates the graphical data to the display device.

The reconstruction subunit 220 includes codes and routines configured to reconstruct a first image and a second image based on the first and second projection datasets, respectively. In one embodiment, the reconstruction subunit 220 includes a set of instructions executable by the processor 205 to provide the functionality for reconstructing the first and second images based on the first and the second projection dataset, respectively. In another embodiment, the reconstruction subunit 220 is stored in the memory 210 and is accessible and executable by the processor 205. In either embodiment, the reconstruction subunit 220 is adapted for communication and cooperation with the processor 205 and the one or more subunits of the imaging unit 200 via the bus 250.

In one embodiment, the reconstruction subunit 220 receives the first and second projection datasets from the communication subunit 215. In such an embodiment, the reconstruction subunit 220 reconstructs the first image and the second image based on the first and second projection datasets respectively using a reconstruction algorithm. The first and second images are three-dimensional (3D) images. Non-limiting examples of the reconstruction algorithm may include a back projection reconstruction algorithm, a filtered back projection reconstruction algorithm, iterative reconstruction algorithm, compressed sensing reconstruction algorithm, few view reconstruction algorithm, or combinations thereof.

In one embodiment, the reconstruction subunit 220 may further generate a cartoon image based on the first image. As used herein the term "cartoon image" is an image where a number of possible intensity values for each voxel in the cartoon image is significantly lesser than a number of possible intensity values for each voxel in the first image. In one example, the number of possible intensity values for each voxel in the first image is 256. In such an example, the cartoon image may be a binary image where the number of possible intensity values for each voxel in the cartoon image is two. In another example, the number of possible intensity values for each voxel in the cartoon image may be three. In yet another example, the number of possible intensity values may be based on a number of material types in the subject. Non-limiting examples of a material type include bone, water, and iodine.

Furthermore, in one embodiment, the reconstruction subunit 220 may generate the cartoon image by thresholding the CT value of each voxel in the first image. In one example, the reconstruction subunit 220 generates a binary image (i.e., the cartoon image) by assigning the value 0 to all voxels with a CT value less than 1500 Hounsfield Units (HU) and by assigning the value 1 to all voxels with a CT value greater than or equal to 1500 HU. The reconstruction subunit 220 is further configured to transmit the first image, the second image, the cartoon image, or combinations thereof to the mask subunit 225 and/or the final image subunit 240.

The mask subunit 225 includes codes and routines configured to identify a metal mask. As used herein, the term "metal mask" refers to one or more voxels in an image that correspond to a metal object (for example, metal implants, dental implants, surgical clips, and the like) within the subject. In one embodiment, the mask subunit 225 includes a set of instructions executable by the processor 205 to provide the functionality for identifying the metal mask. In another embodiment, the mask subunit 225 is stored in the memory 210 and is accessible and executable by the processor 205. In either embodiment, the mask subunit 225 is adapted for communication and cooperation with the processor 205 and the one or more subunits of the imaging unit 200 via the bus 250.

In one embodiment, the mask subunit 225 receives the first image from the reconstruction subunit 220. In such an embodiment, the mask subunit 225 identifies the metal mask in the first image based on a segmentation algorithm. Non-limiting examples of the segmentation algorithm includes a clustering algorithm, an edge detection algorithm, a region growing algorithm, a graph partitioning algorithm, or combinations thereof. In another embodiment, in addition to identifying a metal mask in the first image, the mask subunit 225 may identify a neighborhood mask in the first image. As used herein, the term "neighborhood mask" refers to one or more voxels in an image that surround the metal mask. In one example, the mask subunit 225 identifies one or more voxels within a predetermined distance from the outer surface of the metal mask as the neighborhood mask. The predetermined distance may be specified in terms of metric distance units (for example, 1 millimeter from the surface of the metal mask) or a number of pixels (for example, 10 voxels from the surface of the metal mask). In a further embodiment, the mask subunit 225 receives the first image and the second image from the reconstruction subunit 220. In such an embodiment, the mask subunit 225 identifies at least one of the metal mask and the neighborhood mask in at least one of the first image and the second image.

In yet another embodiment, in addition to identifying a metal mask, the mask subunit 225 may identify one or more material regions in the first image. As used herein the term "material regions" refers to one or more voxels in an image that represent, for example, water, bone, iodine, and the like. In another embodiment, the mask subunit 225 may receive the cartoon image from the reconstruction subunit 220. In such an embodiment, the mask subunit 225 may identify the metal mask, the neighborhood mask, the one or more material regions, or combinations thereof, in the cartoon image based on the segmentation algorithm. Further, the mask subunit 225 may also be configured to transmit the metal mask, the neighborhood mask, the one or more material regions, or combinations thereof to at least one of the reprojection subunit 230, the conversion subunit 235, and the final image subunit 240.

The reprojection subunit 230 includes codes and routines configured to identify a metal trace. As used herein the term "metal trace" refers to one or more dexels in the projection dataset that correspond to the metal object and/or the shadow of the metal object in the subject. In one embodiment, the reprojection subunit 230 includes a set of instructions executable by the processor 205 to provide the functionality for identifying the metal trace in the first projection dataset. In another embodiment, the reprojection subunit 230 is stored in the memory 210 and is accessible and executable by the processor 205. In either embodiment, the reprojection subunit 230 is adapted for communication and cooperation with the processor 205 and the one or more subunits of the imaging unit 200 via the bus 250.

In one embodiment, the reprojection subunit 230 receives the metal mask from the mask subunit 225. In such an embodiment, the reprojection subunit 230 detects a metal trace by reprojecting the metal mask onto the first projection dataset. In another embodiment, the reprojection subunit 230 receives at least one of the first projection dataset and the second projection dataset from the communication subunit 215. In such an embodiment, the reprojection subunit 230 identifies the metal trace directly in at least one of the first projection dataset and the second projection dataset. In another embodiment, the reprojection subunit 230 receives the neighborhood mask and detects a neighborhood trace by reprojecting the neighborhood mask onto the first projection dataset. As used herein the term "neighborhood trace" refers to one or more dexels in the projection dataset that correspond to the neighborhood mask. In yet another embodiment, the reprojection subunit 230 receives one or more material regions and detects one or more material traces by reprojecting the one or more material regions onto the first projection dataset. As used herein, the term "material trace" refers to one or more dexels in the projection dataset that correspond to the one or more material regions. Further, the reprojection subunit 230 transmits at least one of the metal trace, the neighborhood trace, and the one or more material traces to the conversion subunit 235 and/or the final image subunit 240.

The conversion subunit 235 includes codes and routines configured to generate a pseudo dataset at the second energy level. As used herein, the term "pseudo dataset" refers to a dataset at the second energy level that is generated based on at least a portion of the first projection dataset at the first energy level. In one embodiment, the conversion subunit 235 includes a set of instructions executable by the processor 205 to provide the functionality for generating the pseudo dataset at the second energy level. In another embodiment, the conversion subunit 235 is stored in the memory 210 and is accessible and executable by the processor 205. In either embodiment, the conversion subunit 235 is adapted for communication and cooperation with the processor 205 and the one or more subunits of the imaging unit 200 via the bus 250.

In one embodiment, the conversion subunit 235 is configured to receive at least a portion of the first projection dataset from at least one of the communication subunit 215 and the reprojection subunit 230. The conversion subunit 235 generates the pseudo dataset by converting the value of each dexel in at least the portion of the first projection dataset at the first energy level (for example, 160 kVp) to a corresponding value in the second energy level (for example, 120 kVp). In one embodiment, the conversion subunit 235 may convert at least the portion of the first projection dataset to the pseudo dataset based on a projection domain level look-up table. The projection domain look-up table maps one or more dexel values at the first energy level to one or more dexel values at the second energy level. The projection domain look-up table may be defined by, for example, an administrator of the imaging unit 200 based on previously generated clinical data. In another embodiment, the conversion subunit 235 may convert at least the portion of the first projection dataset to the pseudo dataset by generating coefficients based on polynomial fitting. The coefficients map the value of each dexel in at least the portion of the first projection dataset at the first energy level to the pseudo dataset at the second energy level.

In one example, the conversion subunit 235 receives the metal trace at the first energy level from the reprojection subunit 230. In such an example, the conversion subunit 235 generates the pseudo dataset by converting the value of each dexel in the metal trace to a corresponding value at the second energy level. In another example, the conversion subunit 235 receives the metal trace and the neighborhood trace at the first energy level from the reprojection subunit 230. In such an example, the conversion subunit 235 generates the pseudo dataset by converting the value of each dexel in the metal trace and the neighborhood trace to a corresponding value at the second energy level. In yet another example, the conversion subunit 235 receives the first projection dataset at the first energy level from the communication subunit 215. In such an example, the conversion subunit 235 generates the pseudo dataset by converting the value of each dexel in the first projection dataset to a corresponding value at the second energy level.

In another embodiment, the conversion subunit 235 is configured to receive at least a portion of the first image from the reconstruction subunit 220. The conversion subunit 235 generates a pseudo image by converting the value of each voxel in at least the portion of the first image at the first energy level (e.g., 160 kVp) to a corresponding value at the second energy level (e.g., 120 kVp). For example, the conversion subunit 235 may convert at least the portion of the first projection image to the pseudo image based on an image domain look-up table. The image domain look-up table maps one or more voxel values at the first energy level to one or more voxel values at the second energy level. The image domain look-up table may be defined by, for example, an administrator of the imaging unit 200 based on previously generated clinical data. Further, the conversion subunit 235 generates the pseudo dataset by reprojecting the values of each voxel in the pseudo image to the projection domain at the second energy level. In one embodiment, the conversion subunit 235 may be configured to generate the pseudo dataset by transmitting the pseudo image to the reprojection subunit 230. In such an embodiment, the reprojection subunit 230 generates the pseudo dataset by reprojecting the pseudo image onto the projection domain and transmitting the pseudo dataset back to the conversion subunit 235. The conversion subunit 235 is further configured to transmit the pseudo dataset to the final image subunit 240.

The final image subunit 240 includes codes and routines configured to generate the final image of the subject. In one embodiment, the final image subunit 240 includes a set of instructions executable by the processor 205 to provide the functionality for generating the final image of the subject. In another embodiment, the final image subunit 240 is stored in the memory 210 and is accessible and executable by the processor 205. In either embodiment, the final image subunit 240 is adapted for communication and cooperation with the processor 205 and the one or more subunits of the imaging unit 200 via the bus 250.

The final image subunit 240 receives the first projection dataset, the second projection dataset, the pseudo dataset, the metal trace, the neighborhood trace, or combinations thereof from at least one of the subunits of the imaging unit 200. The final image subunit 240 then generates the final image of the subject based on the first projection dataset, the second projection dataset, the pseudo dataset, the metal trace, the neighborhood trace, or combinations thereof, using a reconstruction algorithm. The final image is a 3D image of the subject. The generation of the final image will be described in further detail with reference to FIGS. 3-11. The final image subunit 240 may be further configured to generate graphical data for providing the final image to, for example, a clinician, an operator of the CT scanner, and the like, for diagnosis of the subject. In one embodiment, the final image subunit 240 transmits the graphical data to the display device. In such an embodiment, the display device renders the graphical data and displays the final image. In another embodiment, the final image subunit 240 communicates the graphical data for providing the final image to an operator of the CT scanner, a clinician, and the like, via, for example, an electronic mail, short messaging service, and the like.

FIG. 3 is a flow diagram illustrating an exemplary method 300 for metal artifact reduction, in accordance with aspects of the present specification. The method 300 of FIG. 3 is described with reference to the components of FIG. 2. At step 302, the communication subunit 215 receives a first projection dataset corresponding to X-rays at a first energy level projected towards a subject at a first set of view angles.

At step 304, the communication subunit 215 also receives a second projection dataset corresponding to X-rays at a second energy level projected towards the subject at a second set of view angles. As noted hereinabove, the first energy level is higher than the second energy level. Further, the first set of view angles is different from the second set of view angles. Also, a number of view angles in the first set is lower than a number of view angles in the second set.

Moreover at step 306, the mask subunit 225 identifies a metal trace from at least one of the first projection dataset and the second projection dataset. Further, at step 308, the conversion subunit 235 converts at least a portion of the first projection dataset to a pseudo dataset at the second energy level. Subsequently, at step 310, the final image subunit 240 generates a final image of the subject based on the second projection dataset, the pseudo dataset, and the metal trace. Additionally at step 312, the final image of the subject is visualized on a display device. For example, the final image subunit 240 may generate and transmit graphical data of the final image to a display device. The visualization of the final image may aid, for example, a clinician in diagnosing the subject.

Referring now to FIG. 4, a flow diagram illustrating an exemplary method 400 for metal artifact reduction, in accordance with aspects of the present specification, is depicted. The method 400 of FIG. 4 is described with reference to the components of FIG. 2. At step 402, the communication subunit 215 receives a first projection dataset corresponding to X-rays at a first energy level projected towards a subject at a first set of view angles. Also, at step 404, the communication subunit 215 receives a second projection dataset corresponding to X-rays at a second energy level projected towards the subject at a second set of view angles.

Further, at step 406, the reconstruction subunit 220 reconstructs a first image based on the first projection dataset. For example, the reconstruction subunit 220 may reconstruct the first image based on the first projection dataset using a few view reconstruction algorithm. Also, at step 408, the mask subunit 225 identifies a metal mask and a neighborhood mask from the first image. Moreover, at step 410, the reprojection subunit 230 detects a metal trace and a neighborhood trace in the first projection dataset based on the metal mask and the neighborhood mask respectively.

In addition, as indicated by step 412, the conversion subunit 235 converts at least a portion of the first projection dataset to a pseudo dataset at the second energy level. Subsequently, at step 414, the final image subunit 240 generates a final image of the subject based on the second projection dataset, the pseudo dataset, and the metal trace. For example, the conversion subunit 235 may generate one or more coefficients that map the value of each dexel in the metal trace and the neighborhood trace to the pseudo dataset at the second energy level. In such an example, the one or more coefficients may be determined by fitting the first projection dataset within the neighborhood trace to the second projection dataset within the neighborhood trace. The final image subunit 240 may then replace the values of dexels in the second projection dataset with the values of corresponding dexels in the pseudo dataset that represent the metal trace. Additionally, the final image subunit 240 may generate the final image of the subject based on the second projection dataset that includes the plurality of replaced dexel values using a reconstruction algorithm. Although, FIG. 4 describes a method according to one embodiment that includes generating the final image based on the pseudo dataset including dexels representing the metal trace, in another embodiment, the method may include generating the final image based on a pseudo dataset including dexels representing the metal trace and the neighborhood trace.

Figure 5:
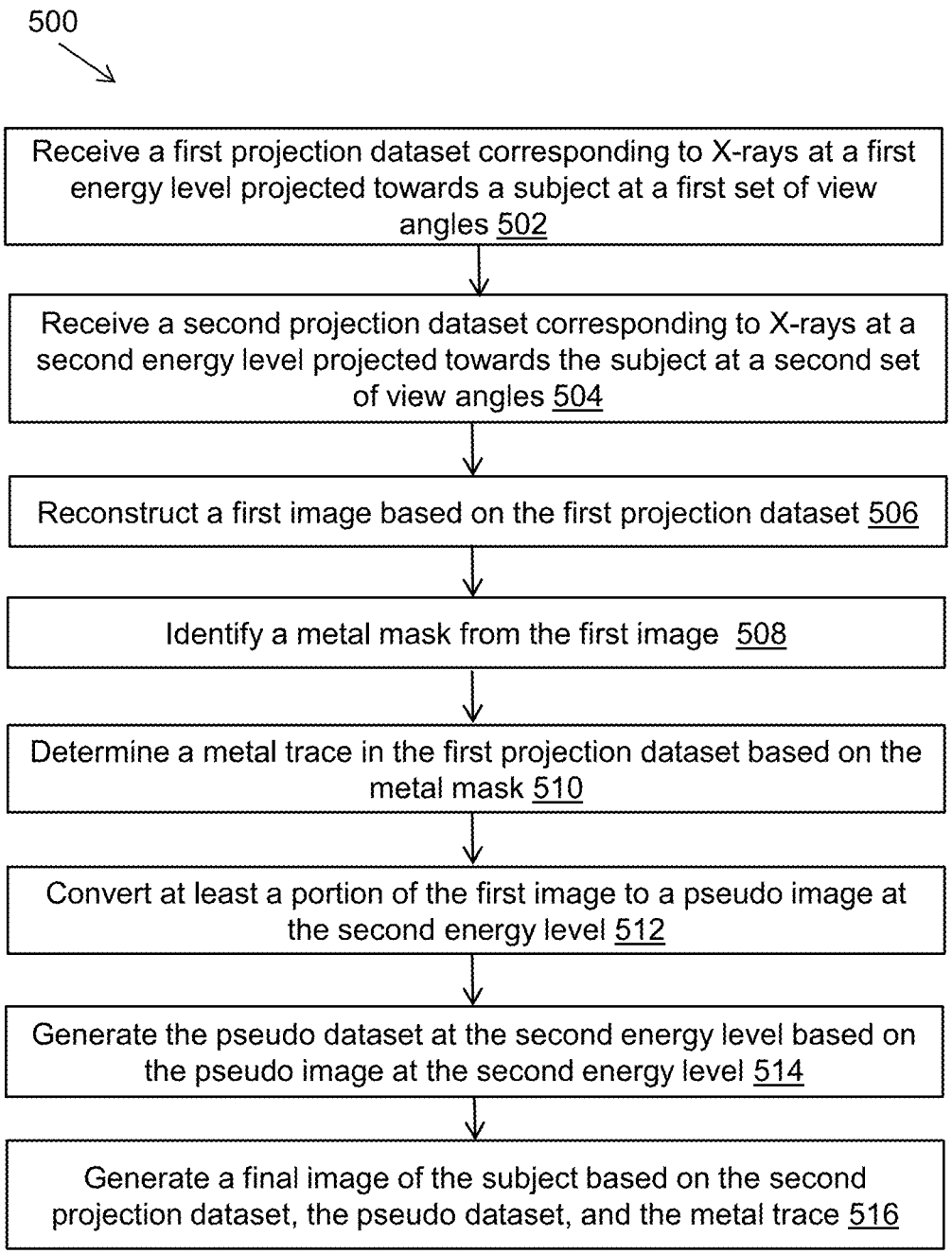

FIG. 5 is a flow diagram illustrating an exemplary method 500 for metal artifact reduction, in accordance with aspects of the present specification. The method 500 of FIG. 5 is described with reference to the components of FIG. 2. At step 502, the communication subunit 215 receives a first projection dataset corresponding to X-rays at a first energy level projected towards a subject at a first set of view angles. Moreover, at step 504, the communication subunit 215 also receives a second projection dataset corresponding to X-rays at a second energy level projected towards the subject at a second set of view angles.

Further, at step 506, the reconstruction subunit 220 reconstructs a first image based on the first projection dataset. Moreover, at step 508, the mask subunit 225 identifies a metal mask from the first image. Subsequently, at step 510, the reprojection subunit 230 determines a metal trace in the first projection dataset based on the metal mask. Also, as indicated by step 512, the conversion subunit 235 converts at least a portion of the first image to a pseudo image at the second energy level. For example, the conversion subunit 235 converts the first image to a pseudo image based on an image domain look-up table. Furthermore, at step 514, the conversion subunit 235 also generates the pseudo dataset at the second energy level based on the pseudo image at the second energy level. Subsequently, at step 516, the final image subunit 240 generates a final image of the subject based on the second projection dataset, the pseudo dataset, and the metal trace.

Figure 6:
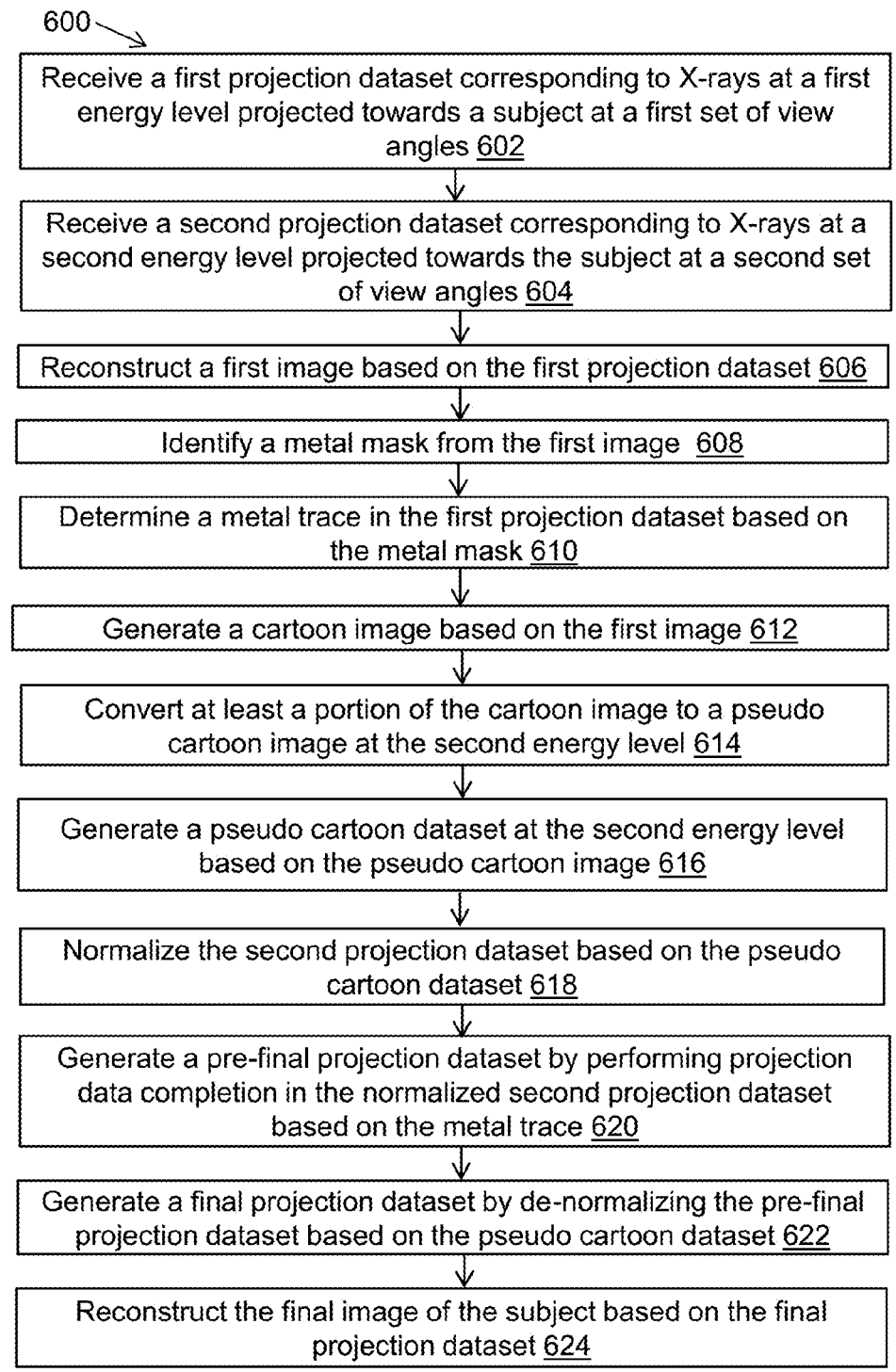

Turning now to FIG. 6, a flow diagram of an exemplary method 600 for metal artifact reduction, in accordance with aspects of the present specification, is illustrated. The method 600 of FIG. 6 is described with reference to the components of FIG. 2. At step 602, the communication subunit 215 receives a first projection dataset corresponding to X-rays at a first energy level projected towards a subject at a first set of view angles. Additionally, at step 604, the communication subunit 215 also receives a second projection dataset corresponding to X-rays at a second energy level projected towards the subject at a second set of view angles. Further, at step 606, the reconstruction subunit 220 reconstructs a first image based on the first projection dataset. Also, at step 608, the mask subunit 225 identifies a metal mask from the first image. Moreover, at step 610, the reprojection subunit 230 determines a metal trace in the first projection dataset based on the metal mask.

Also, as indicated by step 612, the conversion subunit 235 generates a cartoon image based on the first image. For example, the conversion subunit 235 may generate a cartoon image, where the number of possible intensity values for each voxel in the cartoon image is three. Further, at step 614, the conversion subunit 235 converts at least a portion of the cartoon image to a pseudo cartoon image (i.e., pseudo image) at the second energy level. In addition, at step 616, the conversion subunit 235 generates a pseudo cartoon dataset (i.e., pseudo dataset) at the second energy level based on the pseudo cartoon image at the second energy level.

Moreover, at step 618, the final image subunit 240 normalizes the second projection dataset based on the pseudo cartoon dataset. For example, the final image subunit 240 normalizes the second projection dataset by dividing the second projection dataset with the pseudo cartoon dataset. Further, at step 620, the final image subunit 240 generates a pre-final projection dataset by performing projection data completion in the normalized second projection dataset based on the metal trace. Non-limiting examples of projection data completion techniques include linear or cubic spline interpolation, wavelet interpolation, and iterative sinogram in-painting. Furthermore, at step 622, the final image subunit 240 generates a final projection dataset by de-normalizing the pre-final projection dataset based on the pseudo cartoon dataset. For example, the final image subunit 240 de-normalizes the pre-final projection dataset by multiplying the pre-final projection dataset with the pseudo cartoon dataset. Subsequently, at step 624, the final image subunit 240 reconstructs the final image of the subject based on the final projection dataset.

Figure 7:
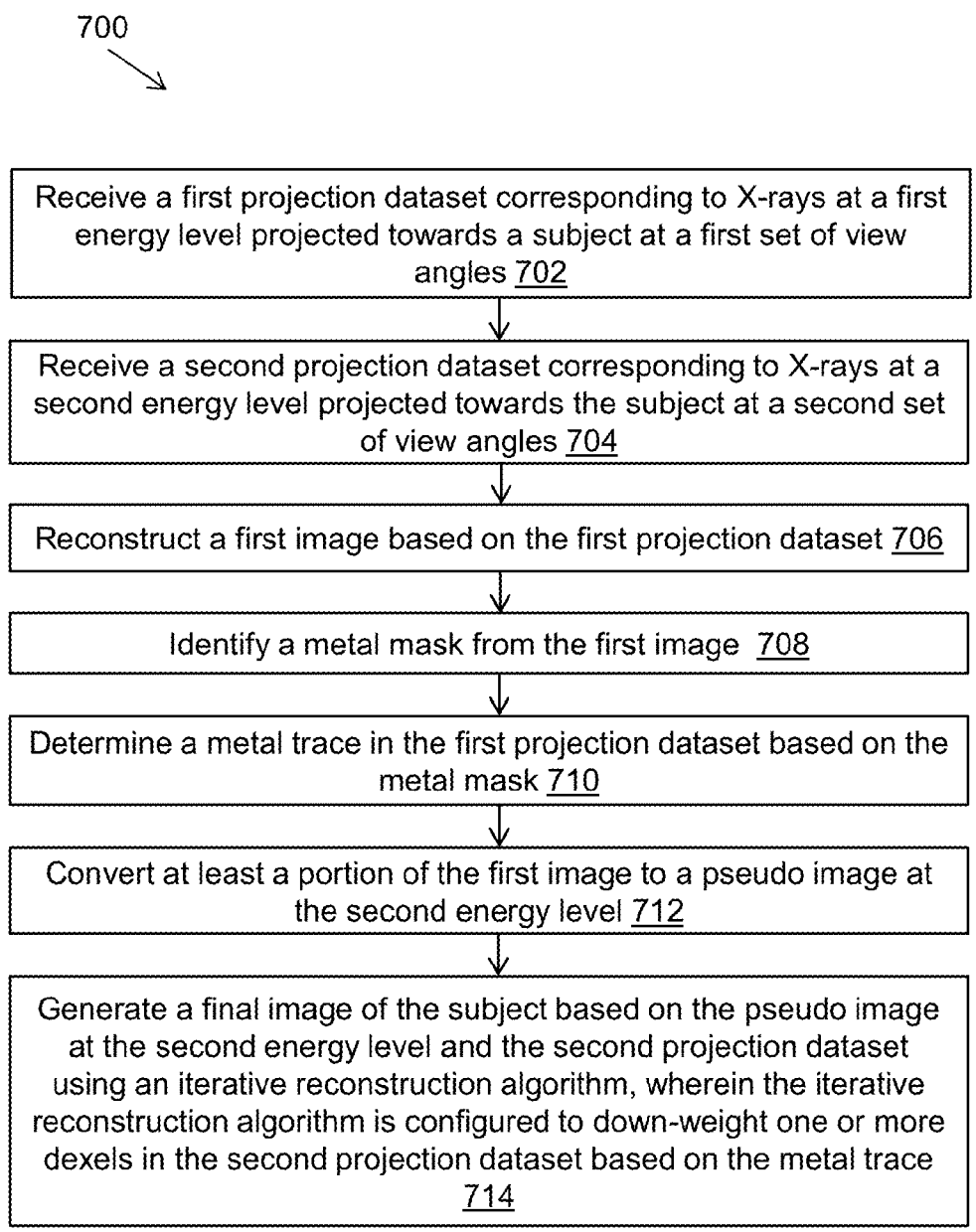

Referring now to FIG. 7, a flow diagram of an exemplary method 700 for metal artifact reduction, in accordance with aspects of the present specification, is illustrated. The method 700 of FIG. 7 is described with reference to the components of FIG. 2. At step 702, the communication subunit 215 receives a first projection dataset corresponding to X-rays at a first energy level projected towards a subject at a first set of view angles. Also, at step 704, the communication subunit 215 receives a second projection dataset corresponding to X-rays at a second energy level projected towards the subject at a second set of view angles.

Moreover, at step 706, the reconstruction subunit 220 reconstructs a first image based on the first projection dataset. Furthermore, at step 708, the mask subunit 225 identifies a metal mask from the first image. Also, at step 710, the reprojection subunit 230 determines a metal trace in the first projection dataset based on the metal mask.

In addition, as indicated by step 712, the conversion subunit 235 converts at least a portion of the first image to a pseudo image at the second energy level. Subsequently, at step 714, the final image subunit 240 generates a final image of the subject based on the pseudo image at the second energy level and the second projection dataset using an iterative reconstruction algorithm. The iterative reconstruction algorithm is configured to down-weight one or more dexels in the second projection dataset based on the metal trace. In one example, the final image subunit 240 generates the final image based on the pseudo image at the second energy level and the second projection dataset using a Prior Image Constrained Compressed Sensing algorithm (i.e., an iterative reconstruction algorithm). In such an example, the final image subunit 240 performs iterative reconstruction of the final image using a datafit term and a prior term. The final image subunit 240 may determine the datafit term by down-weighting one or more dexels corresponding to the metal trace in the second projection dataset and up-weighting one or more dexels corresponding to non-metal trace portions in the second projection dataset. Further, the final image subunit 240 may use the pseudo image at the second energy level as the prior term or constraint/regularization term for the iterative reconstruction of the second projection dataset.

Figure 8:
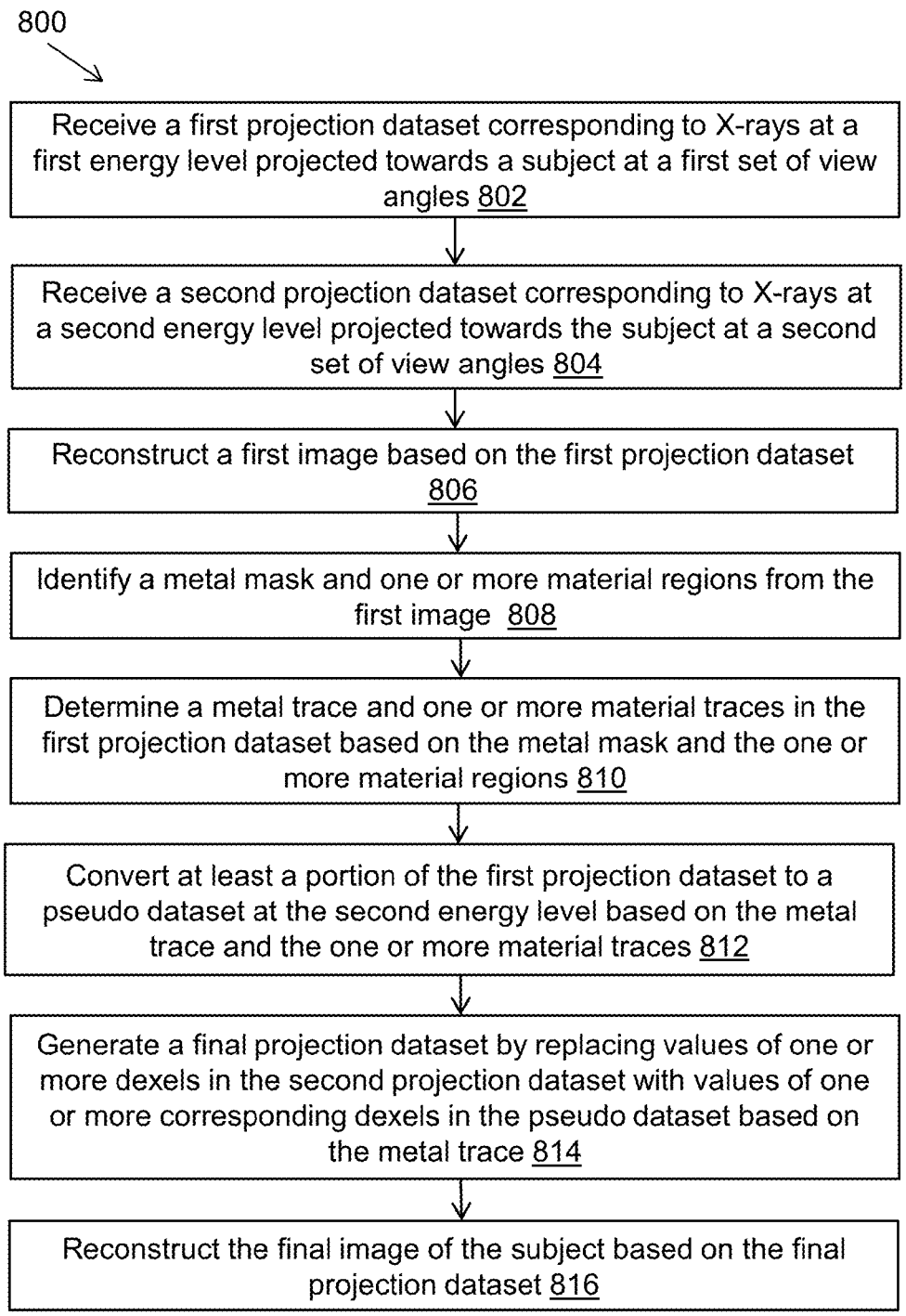

FIG. 8 is a flow diagram of an exemplary method 800 for metal artifact reduction, in accordance with aspects of the present specification. The method 800 of FIG. 8 is described with reference to the components of FIG. 2. At step 802, the communication subunit 215 receives a first projection dataset corresponding to X-rays at a first energy level projected towards a subject at a first set of view angles. Also, at step 804, the communication subunit 215 receives a second projection dataset corresponding to X-rays at a second energy level projected towards the subject at a second set of view angles.

Subsequently, at step 806, the reconstruction subunit 220 reconstructs a first image based on the first projection dataset. Furthermore, at step 808, the mask subunit 225 identifies a metal mask and one or more material regions from the first image. For example, the mask subunit 225 identifies one or more voxels that represent metal, water, and bone regions in a subject. Moreover, at step 810, the reprojection subunit 230 determines a metal trace and one or more material traces in the first projection dataset based on the metal mask and the one or more material regions.

Also, as indicated by step 812, the conversion subunit 235 converts at least a portion of the first projection dataset to a pseudo dataset at the second energy level based on the metal trace and the one or more material traces. For example, the conversion subunit 235 converts the first projection dataset at 160 kVp to a pseudo dataset at 120 kVp using the metal trace and the one or more material traces based on a higher order beam hardening correction algorithm. In such an example, the conversion subunit 235 converts the value of one or more dexels in the first projection dataset at 160 kVp to a corresponding value at 120 kVp based on a physics based model of spectral properties of the metal and the one or more material regions. Moreover, at step 814, the final image subunit 240 generates a final projection dataset by replacing values of one or more dexels in the second projection dataset with values of one or more corresponding dexels in the pseudo dataset based on the metal trace. Subsequently, at step 816, the final image subunit 240 reconstructs the final image of the subject based on the final projection dataset.

Figure 9:
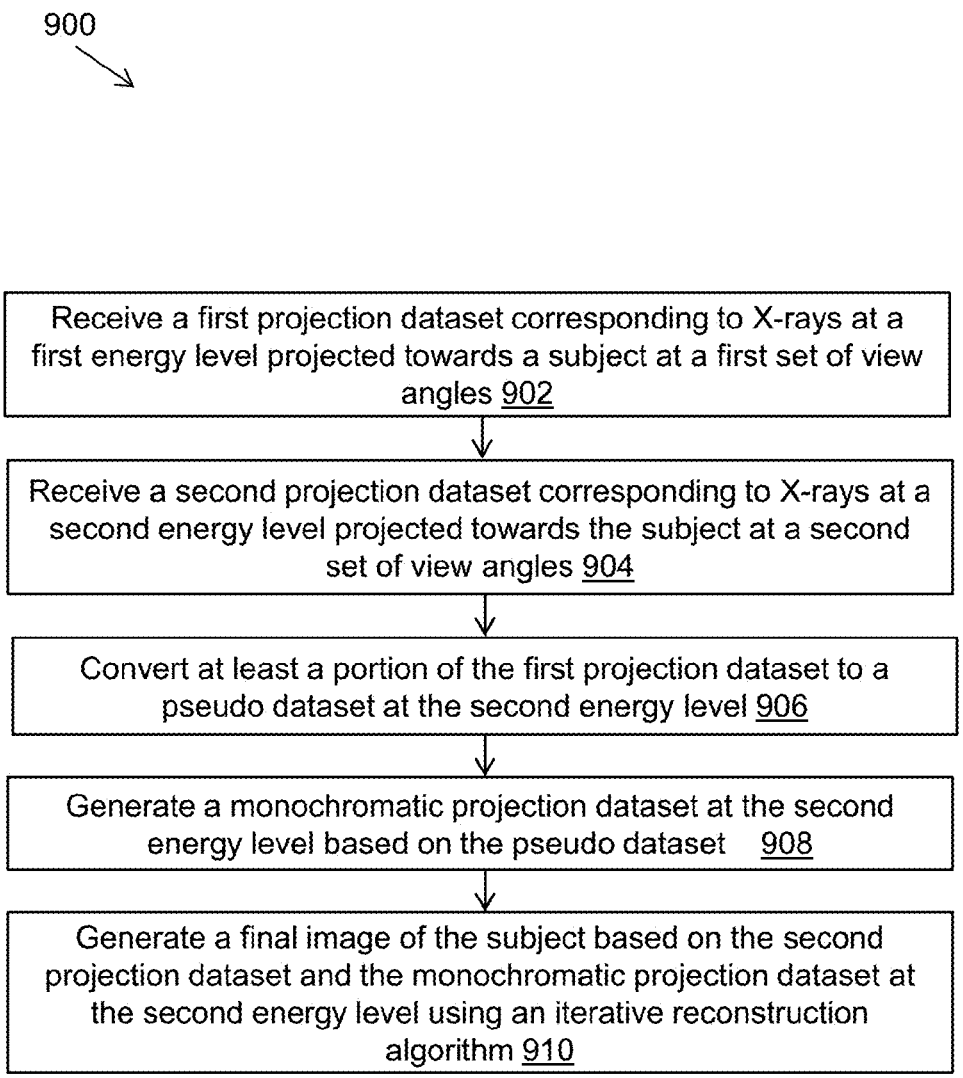

Referring to FIG. 9, a flow diagram of an exemplary method 900 for metal artifact reduction, in accordance with aspects of the present specification, is illustrated. The method 900 of FIG. 9 is described with reference to the components of FIG. 2. At step 902, the communication subunit 215 receives a first projection dataset corresponding to X-rays at a first energy level projected towards a subject at a first set of view angles. Moreover, at step 904, the communication subunit 215 receives a second projection dataset corresponding to X-rays at a second energy level projected towards the subject at a second set of view angles.

Further, at step 906, the conversion subunit 235 converts at least a portion of the first projection dataset to a pseudo dataset at the second energy level. Also, as indicated by step 908, the final image subunit 240 generates a monochromatic projection dataset at the second energy level based on the pseudo dataset. As used herein, the term "monochromatic projection dataset" refers to a projection dataset where the values of the one or more dexels are calibrated to projection values of one or more dexels collected with a monochromatic spectrum at a given energy level. The energy level of the monochromatic spectrum may be expressed in Kilo electron Volts (KeV). In one example, the final image subunit 240 generates the monochromatic projection dataset at the second energy level based on first order water beam hardening correction. In such an example, the monochromatic projection dataset is generated by polynomial fitting based on the attenuation of water.

Subsequently, at step 910, the final image subunit 240 generates a final image of the subject based on the second projection dataset and the monochromatic projection dataset at the second energy level using an iterative reconstruction algorithm. Non-limiting examples of the iterative reconstruction algorithm include a penalized weighted least squares algorithm, a maximum likelihood algorithm, and a maximum a posteriori algorithm. In one example, the second projection dataset and the monochromatic projection dataset are input as a datafit term of the iterative reconstruction algorithm. In such an example, statistical weighting of the iterative reconstruction algorithms may down-weight unreliable data (for example, dexels representing the metal and/or the neighborhood of the metal in the second projection dataset) and up-weight reliable data (for example, dexels representing metal and/or the neighborhood of the metal in the monochromatic projection dataset).

Although in the embodiment of FIG. 9 the final image subunit 240 is described as generating only one monochromatic projection dataset based on the pseudo dataset, in another embodiment, the final image subunit 240 may generate first and second monochromatic projection datasets at the second energy level based on the pseudo dataset and the second projection dataset respectively. In such an embodiment, the final image subunit 240 generates the final image based on the first and second monochromatic projection datasets using the iterative reconstruction algorithm.

Figure 10:
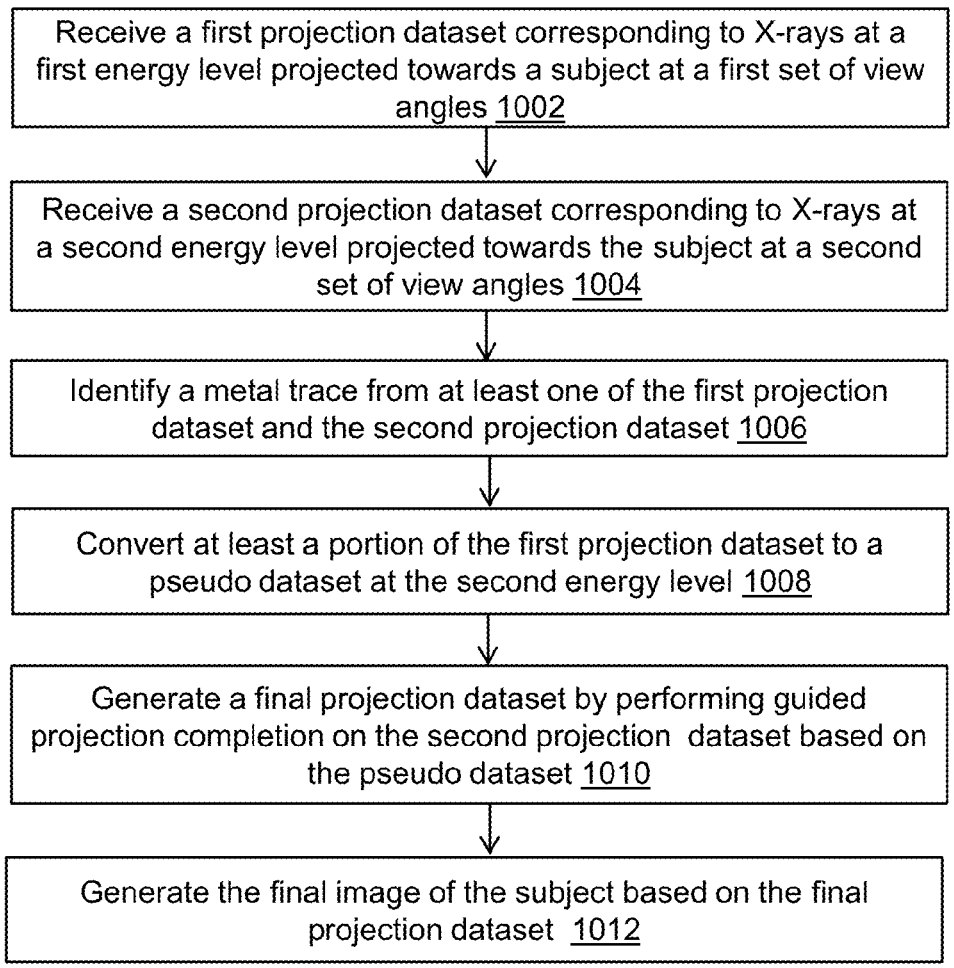

FIG. 10 illustrates a flow diagram of an exemplary method 1000 for metal artifact reduction, in accordance with aspects of the present specification. The method 1000 of FIG. 10 is described with reference to the components of FIG. 2. At step 1002, the communication subunit 215 receives a first projection dataset corresponding to X-rays at a first energy level projected towards a subject at a first set of view angles. Furthermore, at step 1004, the communication subunit 215 receives a second projection dataset corresponding to X-rays at a second energy level projected towards the subject at a second set of view angles.

Moreover, at step 1006, the mask subunit 225 identifies a metal trace from at least one of the first projection dataset and the second projection dataset. Furthermore, at step 1008, the conversion subunit 235 converts at least a portion of the first projection dataset to a pseudo dataset at the second energy level. Also, as indicated by step 1010, the final image subunit 240 generates a final projection dataset by performing guided projection completion on the second projection dataset based on the pseudo dataset. For example, the final image subunit 240 generates the final projection dataset using an iterative in-painting algorithm to complete the second projection dataset using the pseudo dataset as a regularization term. Subsequently, at step 1012 the final image subunit 240 generates the final image of the subject based on the final projection dataset.

Although in the embodiment of FIG. 10, the conversion subunit 235 is described as converting at least a portion of the first projection dataset to a pseudo dataset, in one embodiment the conversion subunit 235 may convert at least the portion of the first projection dataset to a monochromatic projection dataset. In such an embodiment, the final image subunit 240 may generate the final projection dataset by performing guided projection completion on the second projection dataset based on the monochromatic projection dataset. In a further embodiment, the conversion subunit 235 may generate first and second monochromatic projection datasets at the second energy level based on the first projection dataset and the second projection dataset respectively. In such an embodiment, the conversion subunit 235 completes the second projection dataset using the first and second monochromatic projection datasets based on the metal trace by performing guided projection completion.

Figure 11:
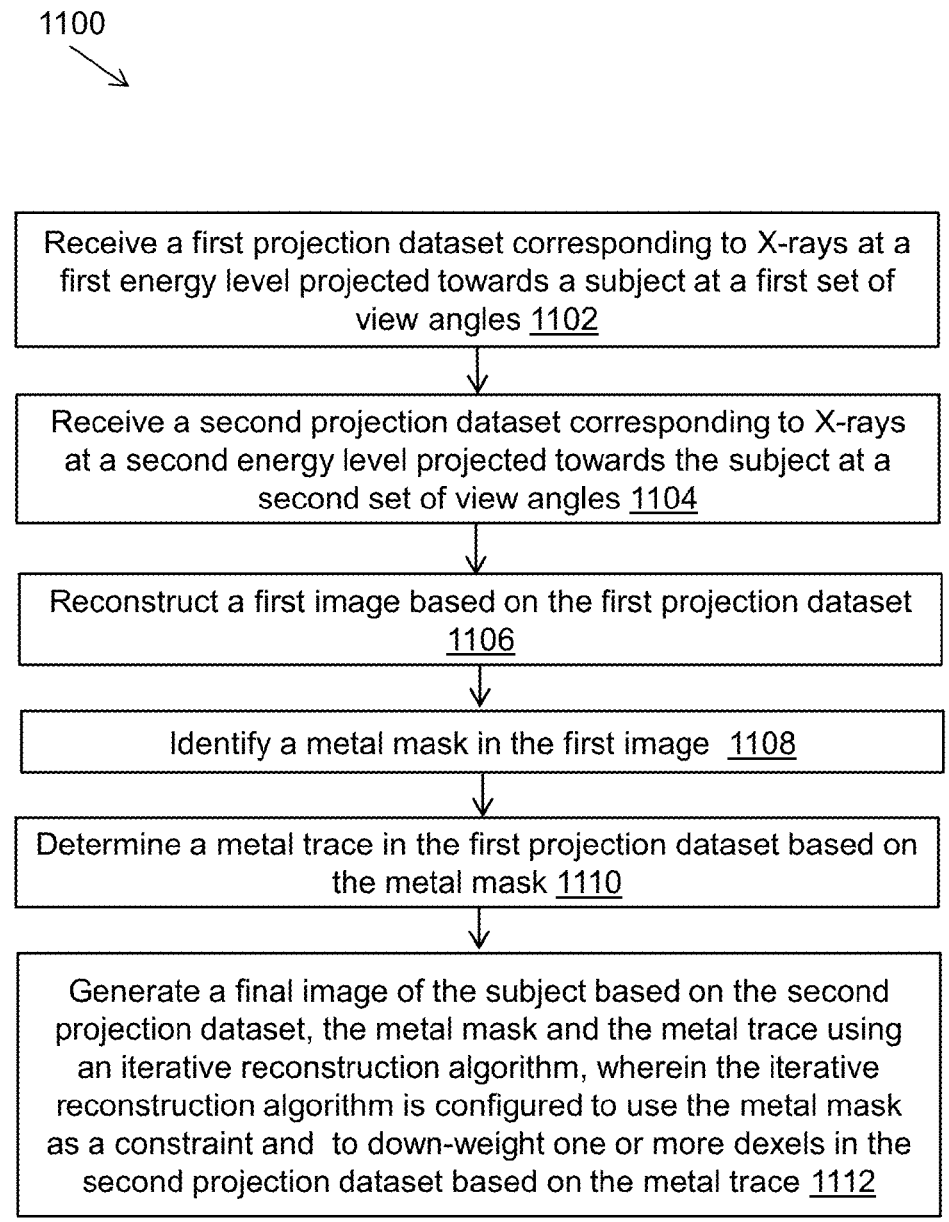

Turning now to FIG. 11, a flow diagram of an exemplary method 1100 for metal artifact reduction, in accordance with aspects of the present specification, is depicted. The method 1100 of FIG. 11 is described with reference to the components of FIG. 2. At step 1102, the communication subunit 215 receives a first projection dataset corresponding to X-rays at a first energy level projected towards a subject at a first set of view angles. Also, at step 1104, the communication subunit 215 receives a second projection dataset corresponding to X-rays at a second energy level projected towards the subject at a second set of view angles. In addition, at step 1106, the reconstruction subunit 220 reconstructs a first image based on the first projection dataset. Furthermore, at step 1108, the mask subunit 225 identifies a metal mask in the first image. Moreover, at step 1110, the reprojection subunit 230 determines a metal trace in the first projection dataset based on the metal mask.

Subsequently, at step 1112, the final image subunit 240 generates a final image of the subject based on the second projection dataset, the metal mask and the metal trace using an iterative reconstruction algorithm. In the embodiment of FIG. 11, the iterative reconstruction algorithm is configured to use the metal mask as a constraint and to down-weight one or more dexels in the second projection dataset based on the metal trace. For example, the final image subunit 240 may iteratively reconstruct the final image based on the second projection dataset using the shape or the circumference of the metal mask as a constraint.

Figure 12:
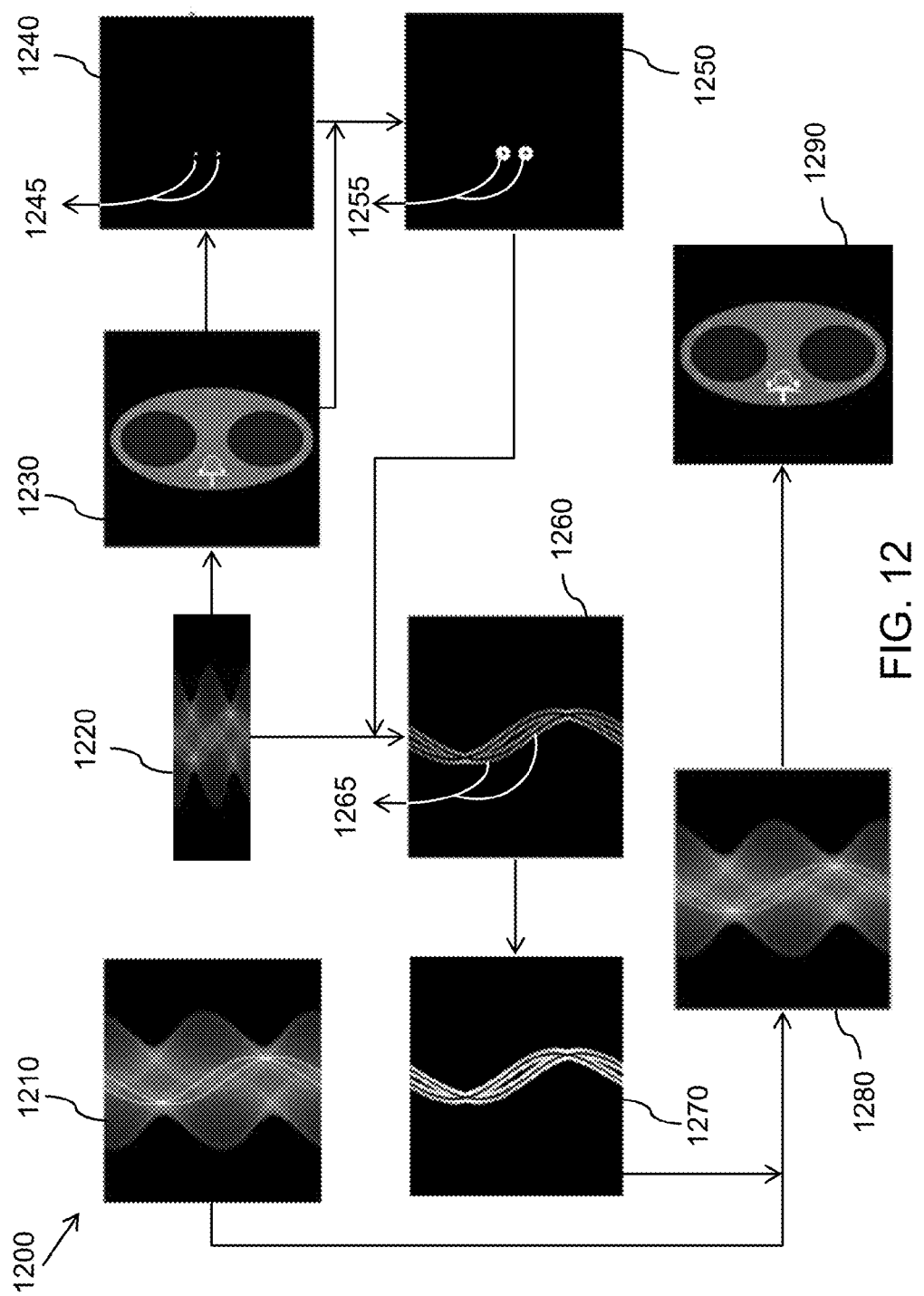
FIG. 12 is a schematic representation illustrating an exemplary method for metal artifact reduction, in accordance with aspects of the present specification.

Referring now to FIG. 12, a schematic representation of an exemplary method 1200 for metal artifact reduction, in accordance with aspects of the present specification, is depicted. The method 1200 of FIG. 12 is described with reference to the components of FIG. 2. The communication subunit 215 receives a first projection dataset 1220 corresponding to X-rays at 180 kVp (i.e., a first energy level) projected towards a phantom (i.e., a subject) at a first set of view angles. In the illustrated embodiment, the phantom includes metal, water, and air. The communication subunit 215 also receives a second projection dataset 1210 corresponding to X-rays at 120 kVp (i.e., a second energy level) projected towards the subject at a second set of view angles. In this example, the number of view angles in the first set of view angles is 180 and the number of view angles in the second set is 720. The reconstruction subunit 220 reconstructs a first image 1230 based on the first projection dataset 1220 using, for example, a few view reconstruction algorithm.

Further, the mask subunit 225 identifies a metal mask 1240 and a neighborhood mask 1250 from the first image 1230. For example, the mask subunit 225 identifies a plurality of voxels 1245 that represent metal and a plurality of voxels 1255 that represent a neighborhood of the metal in the first image 1230 based on a segmentation algorithm. Additionally, the reprojection subunit 230 detects a metal trace and a neighborhood trace 1260 in the first projection dataset 1220 based on the metal mask 1240 and the neighborhood mask 1250 respectively. For example, the reprojection subunit 230 identifies a plurality of dexels 1265 in the first projection dataset 1220 that represent the metal trace and the neighborhood trace 1260 by reprojecting the plurality of voxels 1245 and 1255 that respectively represent the metal mask 1240 and the neighborhood mask 1250. In this example, since the number of view angles corresponding to the first projection dataset 1220 is lesser than the number of view angles corresponding to the second projection dataset 1210, the reprojection subunit 230 may up-sample the metal trace and/or the neighborhood trace 1260 to obtain a dataset which corresponds to the number of view angles of the second projection dataset 1210. In one example, the reprojection subunit 230 may up-sample the metal trace and/or the neighborhood trace based on view interpolation.

Moreover, the conversion subunit 235 generates a pseudo dataset 1270 at 120 kVp based on the metal trace and the neighborhood trace 1260. For example, the conversion subunit 235 generates the pseudo dataset 1270 by converting the values corresponding to the one or more dexels 1265 of the metal trace and the neighborhood trace 1260 at 180 kVp to values at 120 kVp using coefficients generated based on polynomial fitting. Further, the final image subunit 240 generates a final projection dataset 1280 at 120 kVp based on the second projection dataset 1210 at 120 kVp and the pseudo dataset 1270 at 120 kVp. For example, the final image subunit 240 generates the final projection dataset 1280 by replacing dexel values in the second projection dataset 1210 with corresponding dexel values in the pseudo dataset 1270. Subsequently, the final image subunit 240 reconstructs a final image 1290 of the phantom based on the final projection dataset 1280.

The systems and methods for metal artifact reduction that are described hereinabove are advantageous compared to currently available systems and methods. Typically, the first projection dataset is less corrupted due to metal objects present in the subject, since the X-rays generated at the first energy level (for example, 160 kVp, 180 kVp, and the like) have stronger penetration through the metal objects. As described hereinabove, the pseudo dataset is generated based on the first projection dataset at the first energy level. Thus, the final image generated based on the first projection dataset and the pseudo dataset as described hereinabove has significantly fewer metal artifacts compared to a final image generated using currently available metal artifact reduction methods. Moreover, since the first projection dataset is generated based on X-rays projected at a limited number of view angles, the subject's exposure to the X-rays at the first energy level is advantageously maintained at a minimum level.

It is to be understood that not necessarily all such objects or advantages described above may be achieved in accordance with any particular implementation. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the technology has been described in detail in connection with only a limited number of implementations, it should be readily understood that the invention is not limited to such disclosed implementations. Rather, the technology can be modified to incorporate any number of variations, alterations, substitutions or equivalent arrangements not heretofore described, but which are commensurate with the spirit and scope of the disclosure. Additionally, while various implementations of the technology have been described, it is to be understood that aspects of the technology may include only some of the described implementations. Accordingly, the inventions are not to be seen as limited by the foregoing description, but are only limited by the scope of the appended claims.

What is claimed as new and desired to be protected by Letters Patent of the United States is:

1. A method, comprising:
    receiving, with at least one processor, a first projection dataset corresponding to X-rays at a first energy level projected towards a subject at a first set of view angles;
    receiving, with the at least one processor, a second projection dataset corresponding to X-rays at a second energy level projected towards the subject at a second set of view angles;
    identifying, with the at least one processor, a metal trace from at least one of the first projection dataset and the second projection dataset;
    converting, with the at least one processor, at least a portion of the first projection dataset to a pseudo dataset at the second energy level; and
    generating, with the at least one processor, a final image of the subject based on the second projection dataset, the pseudo dataset, and the metal trace.

2. The method of claim 1, wherein the first set of view angles is different from the second set of view angles, and wherein a number of view angles in the first set is lower than a number of view angles in the second set.

3. The method of claim 1, wherein identifying the metal trace comprises:
    reconstructing a first image based on the first projection dataset;
    segmenting a metal mask from the first image; and
    determining the metal trace in the first projection dataset based on the metal mask.

4. The method of claim 3, wherein converting at least the portion of the first projection dataset to the pseudo dataset at the second energy level comprises:
    converting at least a portion of the first image to a pseudo image at the second energy level; and
    generating the pseudo dataset at the second energy level based on the pseudo image at the second energy level.

5. The method of claim 3, wherein converting at least the portion of the first projection dataset to the pseudo dataset at the second energy level comprises:
    segmenting one or more material regions from the first image; and
    generating the pseudo dataset at the second energy level based on the one or more material regions and the first projection dataset using a higher order beam hardening correction technique.

6. The method of claim 3, wherein generating the final image of the subject comprises:
    generating a final projection dataset by replacing one or more dexels in the second projection dataset with one or more dexels in the pseudo dataset based on the metal trace; and
    reconstructing the final image of the subject based on the final projection dataset.

7. The method of claim 3, wherein converting at least the portion of the first projection dataset to the pseudo dataset at the second energy level comprises:
    generating a cartoon image based on the first image;
    converting at least a portion of the cartoon image to a pseudo image at the second energy level; and
    generating the pseudo dataset at the second energy level based on the pseudo image at the second energy level.

8. The method of claim 7, wherein generating the final image of the subject comprises:
    normalizing the second projection dataset based on the pseudo dataset;
    generating a pre-final projection dataset by replacing one or more dexels in the normalized second projection dataset with one or more dexels in the pseudo dataset based on the metal trace;
    generating a final projection dataset by de-normalizing the pre-final projection dataset based on the pseudo dataset; and
    reconstructing the final image of the subject based on the final projection dataset.

9. The method of claim 3, wherein generating the final image of the subject comprises:
    segmenting a neighborhood mask from the first image based on the metal mask;

identifying a neighborhood trace in the first projection dataset based on the neighborhood mask;

generating a final projection dataset by replacing one or more dexels in the second projection dataset with one or more dexels in the pseudo dataset based on the metal trace and the neighborhood trace; and reconstructing the final image of the subject based on the final projection dataset.

10. The method of claim 1, wherein generating the final image of the subject comprises:

reconstructing a first image based on the first projection dataset;

converting at least a portion of the first image to a pseudo image at the second energy level; and generating the final image of the subject based on the pseudo image at the second energy level and the second projection dataset using an iterative reconstruction technique, wherein the iterative reconstruction technique is configured to down-weight one or more dexels in the second projection dataset based on the metal trace.

11. The method of claim 1, wherein generating the final image of the subject comprises:

generating a monochromatic projection dataset at the second energy level based on the pseudo dataset; and generating the final image of the subject based on the monochromatic projection dataset and the second projection dataset using an iterative reconstruction technique, wherein the iterative reconstruction technique is configured to down-weight one or more dexels in the second projection dataset based on the metal trace.

12. The method of claim 1, wherein generating the final image of the subject comprises:

generating a final projection dataset by performing guided projection completion in the second projection dataset based on the pseudo dataset; and generating the final image of the subject based on the final projection dataset.

13. A system, comprising:

at least one processor;

a communication subunit configured to:
  receive a first projection dataset corresponding to X-rays at a first energy level projected towards a subject at a first set of view angles; and
  receive a second projection dataset corresponding to X-rays at a second energy level projected towards the subject at a second set of view angles;

a mask subunit communicatively coupled with the communication subunit and configured to identify a metal trace from at least one of the first projection dataset and the second projection dataset;

a conversion subunit communicatively coupled with the mask subunit and configured to convert at least a portion of the first projection dataset to a pseudo dataset at the second energy level; and a final image subunit communicatively coupled with the conversion subunit and configured to generate a final image of the subject based on the second projection dataset, the pseudo dataset, and the metal trace, wherein one or more of the communication subunit, the mask subunit, the conversion subunit, and the final image subunit are executable by the at least one processor.

14. The system of claim 13, wherein the first set of view angles is different from the second set of view angles and a number of view angles in the first set is lower than a number of view angles in the second set.

15. The system of claim 13, further comprising a reconstruction subunit configured to:

reconstruct a first image based on the first projection dataset; and generate a cartoon image based on the first image.

16. The system of claim 15, wherein the mask subunit is further configured to segment at least one of a metal mask and a neighborhood mask from at least one of the first image and the cartoon image.

17. The system of claim 16, further comprising a reprojection subunit configured to:

identify the metal trace in the first projection dataset based on the metal mask; and identify a neighborhood trace in the first projection dataset based on the neighborhood mask.

18. The system of claim 17, wherein the conversion subunit is further configured to generate the pseudo dataset at the second energy level based on one or more material regions in the first image, the metal trace, and the first projection dataset using a higher order beam hardening correction technique.

19. The system of claim 17, wherein the conversion subunit is further configured to:

convert at least one of at least a portion of the first image and at least a portion of the cartoon image to a pseudo image at the second energy level; and generate the pseudo dataset at the second energy level based on the pseudo image at the second energy level.

20. The system of claim 18, wherein the final image subunit is further configured to:

generate a final projection dataset by replacing one or more dexels in the second projection dataset with one or more dexels in the pseudo dataset based on at least one of the metal trace and the neighborhood trace; and reconstruct the final image of the subject based on the final projection dataset.

21. The system of claim 18, wherein the final image subunit is further configured to generate the final image of the subject based on the pseudo image at the second energy level and the second projection dataset using an iterative reconstruction technique, and wherein the iterative reconstruction technique is configured to down-weight one or more dexels in the second projection dataset based on the metal trace.

22. The system of claim 13, wherein the conversion subunit is further configured to generate a monochromatic projection dataset at the second energy level based on the pseudo dataset.

23. The system of claim 22, wherein the final image subunit is further configured to generate the final image of the subject based on the monochromatic projection dataset and the second projection dataset using an iterative reconstruction technique, and wherein the iterative reconstruction technique is configured to down-weight one or more dexels in the second projection dataset based on the metal trace.

24. An imaging system, comprising:

a computed tomography (CT) scanner configured to:
  project X-rays at a first energy level towards a subject at a first set of view angles;
  project X-rays at a second energy level towards the subject at a second set of view angles;
  generate a first projection dataset corresponding to the X-rays at the first energy level;
  generate a second projection dataset corresponding to the X-rays at the second energy level;

a controller communicatively coupled to the CT scanner and comprising:

at least one processor;

a communication subunit configured to receive the first projection dataset and the second projection dataset from the CT scanner;

a mask subunit communicatively coupled with the communication subunit and configured to identify a metal trace from at least one of the first projection dataset and the second projection dataset;

a conversion subunit communicatively coupled with the mask subunit and configured to convert at least a portion of the first projection dataset to a pseudo dataset at the second energy level; and a final image subunit communicatively coupled with the conversion subunit and configured to generate a final image of the subject based on the second projection dataset, the pseudo dataset, and the metal trace, wherein one or more of the communication subunit, the mask subunit, the conversion subunit, and the final image subunit are executable by the at least one processor.

25. A computer program product comprising a non-transitory computer readable medium encoding instructions that, in response to execution by at least one processor, cause the at least one processor to perform operations comprising:

receiving a first projection dataset corresponding to X-rays at a first energy level projected towards a subject at a first set of view angles;

receiving a second projection dataset corresponding to X-rays at a second energy level projected towards the subject at a second set of view angles;

identifying a metal trace from at least one of the first projection dataset and the second projection dataset;

converting at least a portion of the first projection dataset to a pseudo dataset at the second energy level; and generating a final image of the subject based on the second projection dataset, the pseudo dataset, and the metal trace.

* * * * *